US009734286B2

(12) United States Patent
Ramanathan (10) Patent No.: US 9,734,286 B2
(45) Date of Patent: Aug. 15, 2017

(54) SYSTEM AND METHOD FOR SPLITTING DICOM MEDICAL IMAGE SERIES INTO FRAMESETS

(71) Applicant: RamSoft Inc., Toronto (CA)

(72) Inventor: Vijay Ramanathan, Toronto (CA)

(73) Assignee: RamSoft Inc., Toronto (CA)

( * ) Notice: Subject to any disclaimer, the term of this patent is extended or adjusted under 35 U.S.C. 154(b) by 0 days.

(21) Appl. No.: 14/954,939

(22) Filed: Nov. 30, 2015

(65) Prior Publication Data
US 2016/0154933 A1 Jun. 2, 2016

Related U.S. Application Data

(60) Provisional application No. 62/085,479, filed on Nov. 28, 2014.

(51) Int. Cl.
| | | |
|---|---|---|
| *G06F 19/00* | (2011.01) | |
| *A61B 8/08* | (2006.01) | |
| *G06T 7/00* | (2017.01) | |
| *G06F 17/00* | (2006.01) | |
| *H04N 5/76* | (2006.01) | |

(52) U.S. Cl.
CPC .......... *G06F 19/321* (2013.01); *A61B 8/5292* (2013.01); *G06F 17/00* (2013.01); *G06T 7/0012* (2013.01); *H04N 5/76* (2013.01)

(58) Field of Classification Search
CPC ..... G06F 19/321; G06F 17/00; G06T 7/0012; G06K 9/36; H04N 5/76; A61B 8/5292; A61B 8/52924
See application file for complete search history.

(56) References Cited

U.S. PATENT DOCUMENTS

| | | | | | |
|---|---|---|---|---|---|
| 5,671,353 | A | * | 9/1997 | Tian | G06F 19/321 714/37 |
| 6,894,707 | B2 | * | 5/2005 | Nemoto | A61B 6/032 345/184 |
| 7,162,623 | B2 | * | 1/2007 | Yngvesson | G06T 1/00 345/619 |
| 7,177,453 | B2 | * | 2/2007 | Suryanarayanan | G06T 7/0012 382/128 |
| 7,260,249 | B2 | * | 8/2007 | Smith | G06T 7/0012 378/28 |
| 7,283,654 | B2 | * | 10/2007 | McLain | G06T 5/009 382/128 |

(Continued)

*Primary Examiner* — Manav Seth
(74) *Attorney, Agent, or Firm* — Sheppard, Mullin, Richter & Hampton LLP (57) ABSTRACT

Systems and methods are described for splitting DICOM medical image series into framesets. In one implementation, a method of splitting a DICOM medical image series into framesets includes determining that a first DICOM image object of the DICOM medical image series is the first DICOM object of the medical image series and creating a first frame set including the first DICOM image object in response to determining that the first DICOM image object is the first DICOM object of the medical image series. In subsequent steps, the method may include determining that a second DICOM image object of the DICOM medical image series does not have more than one image frame; and determining whether a first predefined DICOM tag of interest of the second DICOM image object matches a first DICOM tag of interest of a first image of the first frameset.

18 Claims, 6 Drawing Sheets

(56) References Cited

U.S. PATENT DOCUMENTS

| | | | | |
|---|---|---|---|---|
| 7,574,452 B2* | 8/2009 | Keen | ................. | G06F 19/321 |
| 7,602,179 B2* | 10/2009 | van der Kouwe | ... | G01R 33/561 |
| | | | | 324/307 |
| 7,660,488 B2* | 2/2010 | Reicher | ................. | G06F 19/321 |
| | | | | 345/660 |
| 7,979,522 B2* | 7/2011 | Lunsford | ............. | G06F 19/321 |
| | | | | 709/223 |
| 8,086,077 B2* | 12/2011 | Eichhorn | ............ | G06F 17/3028 |
| | | | | 382/240 |
| 8,140,350 B2* | 3/2012 | Rothpearl | ......... | G06F 17/30265 |
| | | | | 705/2 |
| 8,145,503 B2* | 3/2012 | Backhaus | ............ | G06F 19/321 |
| | | | | 705/2 |
| 8,233,750 B2* | 7/2012 | Minakuchi | ............ | G06F 19/321 |
| | | | | 382/128 |
| 8,254,649 B2* | 8/2012 | Matsue | ................. | G06F 19/321 |
| | | | | 382/128 |
| 8,781,261 B2* | 7/2014 | Eichhorn | ............ | G06F 17/3028 |
| | | | | 382/305 |
| 8,879,807 B2* | 11/2014 | Fram | ..................... | A61B 6/463 |
| | | | | 382/128 |
| 8,954,884 B1* | 2/2015 | Barger | ................. | G06F 3/0485 |
| | | | | 705/3 |
| 8,976,190 B1* | 3/2015 | Westerhoff | ............. | G06T 19/20 |
| | | | | 345/424 |
| 2005/0065424 A1* | 3/2005 | Shah | ..................... | A61B 6/463 |
| | | | | 600/407 |

* cited by examiner

SYSTEM AND METHOD FOR SPLITTING DICOM MEDICAL IMAGE SERIES INTO FRAMESETS

CROSS-REFERENCE TO RELATED APPLICATIONS

This application claims the benefit of U.S. Provisional Application No. 62/085,479 filed on Nov. 28, 2014, which is incorporated herein by reference in its entirety.

TECHNICAL FIELD

The present disclosure relates generally to Digital Imaging and Communications in Medicine (DICOM) image series, and more particularly, some embodiments relate to systems and methods for splitting DICOM medical image series into framesets.

DESCRIPTION OF THE RELATED ART

Diagnostic medical imaging is the process of creating visual representations of a body's interior for the purpose of medical diagnosis and intervention. The diagnostic medical images may be captured by various modalities using various imaging techniques such as magnetic resonance imaging (MRI), X-ray radiography, computed tomography, nuclear medicine scans, ultrasound, etc. Image data management systems for communicating, storing, and managing the diagnostic imaging data continue to grow in use.

Conventionally, medical image studies for a particular patient are sorted and reordered by a quality control technologist. While human technologist may order the image studies in a predetermined format, such methods are inefficient and cumbersome. Particularly, such methods may not conform to a particular physician, modality, or medical facility's preferences for the image studies. Moreover, such methods are subject to human error.

BRIEF SUMMARY OF THE DISCLOSURE

According to various embodiments of the technology disclosed herein, systems and methods are disclosed for splitting DICOM medical image series into framesets. In one embodiment, a method of splitting a DICOM medical image series into framesets includes receiving a DICOM medical image series at a non-transitory computer readable medium. In implementations of this embodiment, one or more processors execute computer-readable instructions that cause a DICOM computing system to: determine that a DICOM image object of the DICOM medical image series is not a first DICOM object of the medical image series; determine that the DICOM image object does not have more than one image frame; and determine whether a first predefined DICOM tag of interest of the DICOM image object matches a first DICOM tag of interest of a first image of a first frameset.

In implementations where it is determined that the first predefined DICOM tag of interest of the DICOM image object matches the first DICOM tag of interest of the first image of the frameset, the one or more processors are configured to add the DICOM image object to the first frameset. In implementations where it is determined that the first predefined DICOM tag of interest of the DICOM image object does not match the first DICOM tag of interest of the first image of the frameset, the one or more processors are configured to create a second frame set including the DICOM image object.

In one embodiment, prior to determining that a DICOM image object of the DICOM medical image series is not the first DICOM object of the medical image series, the method includes: determining that a first DICOM image object of the DICOM medical image series is the first DICOM object of the medical image series; and creating the first frame set including the first DICOM image object in response to determining that the first DICOM image object is the first DICOM object of the medical image series.

In various implementations, prior to splitting a DICOM medical image series into framesets, a user predefines DICOM tags of interest that are made unique for all frames (images) within each frameset that is created from the received DICOM medical image series.

Other features and aspects of the disclosed method will become apparent from the following detailed description, taken in conjunction with the accompanying drawings, which illustrate, by way of example, the features in accordance with embodiments of the disclosure. The summary is not intended to limit the scope of the claimed disclosure, which is defined solely by the claims attached hereto.

BRIEF DESCRIPTION OF THE DRAWINGS

The figures are provided for purposes of illustration only and merely depict typical or example embodiments. They do not limit the breadth, scope, or applicability of the invention.

DETAILED DESCRIPTION

In accordance with the present disclosure, systems and methods are provided for implementing a user-configurable rules based engine for a DICOM viewing application that automatically splits a DICOM image series into framesets. In one embodiment, a user (e.g. physician, facility, etc.) may define which DICOM tags may be unique for all frames (images) within a frameset. In one particular embodiment, a graphical user interface (GUI) is provided for implementing the rules based engine for splitting a DICOM image series into framesets. Although the disclosed methods are described with reference to a DICOM viewing application, in alternative embodiments they may be implemented in other DICOM applications, such as, for example, the transmission and storage of DICOM image series.

Figure 1:
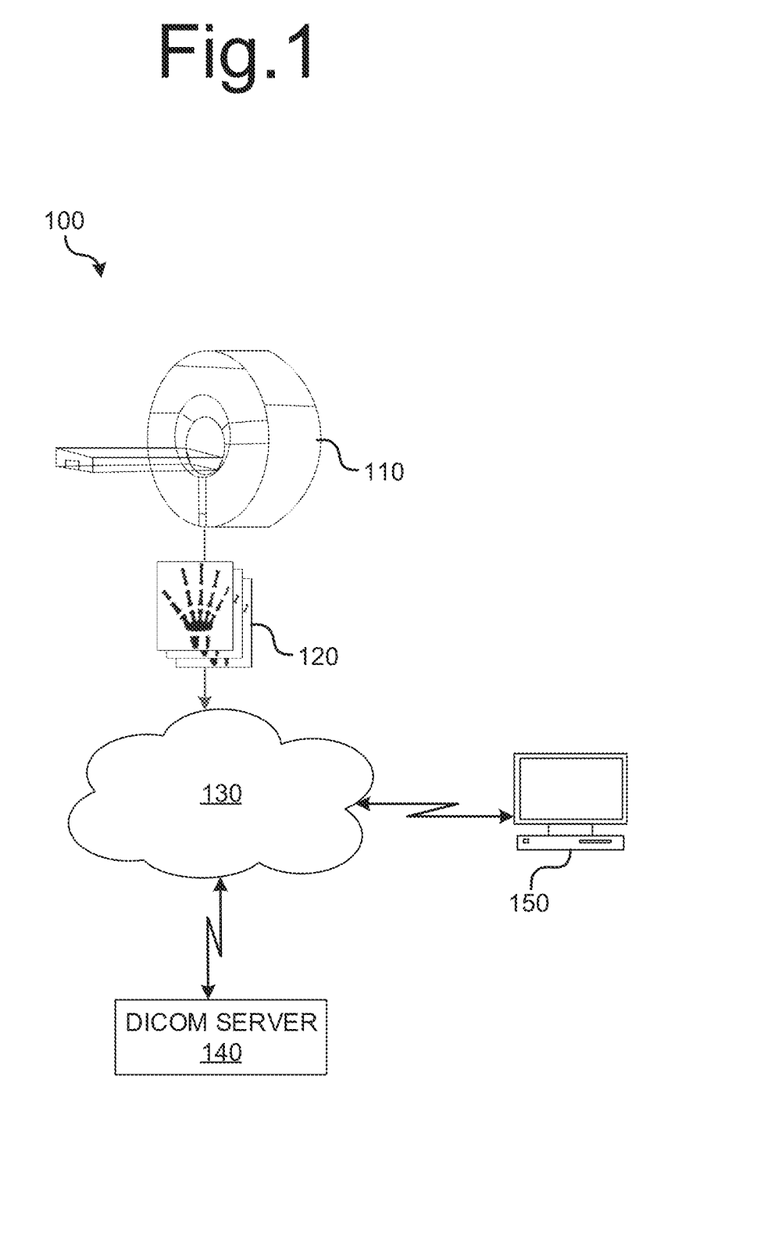
FIG. 1 illustrates an example environment for implementing the systems and methods of the present disclosure.

Before describing the invention in detail, it is useful to describe an example communications environment in which the invention can be implemented. FIG. 1 illustrates such an example communications environment 100. In example environment 100, a patient undergoes a diagnostic imaging study at an imaging facility using medical modality 110. During the medical imaging study, a medical image series 120 and other related diagnostic information is generated. For example, modality may apply magnetic resonance imaging (MRI), an X-ray radiography, computed tomography, nuclear medicine scans, ultrasound, or other techniques to generate the medical image series 120.

In this exemplary environment 100, the generated image series 120 follow the Digital Imaging and Communications in Medicine (DICOM) standard for handling, storing, printing, managing and communicating medical imaging information. Under the DICOM standard, medical image information is grouped into a collection of data attributes that define a DICOM data object. A DICOM data object may include data attributes such as image pixel data (corresponding to the medical image or images), patient name, patient ID, patient birth, modality information, diagnostic imaging study information, etc. Each of the data attributes includes a tag identifier (including group number and element number), and tag values including data about the associated tag.

Tags are used to identify and group diagnostic images into series 120. Software applications executed by a DICOM computer 150 may subsequently display the series of images. The medical image studies are separated into series (sequences) by the imaging equipment modalities 110, largely based on acquisition parameters. Each series of images 120 consists of one or more medical image DICOM objects and each DICOM object may be a single frame image or a multi-frame image.

Figure 2:
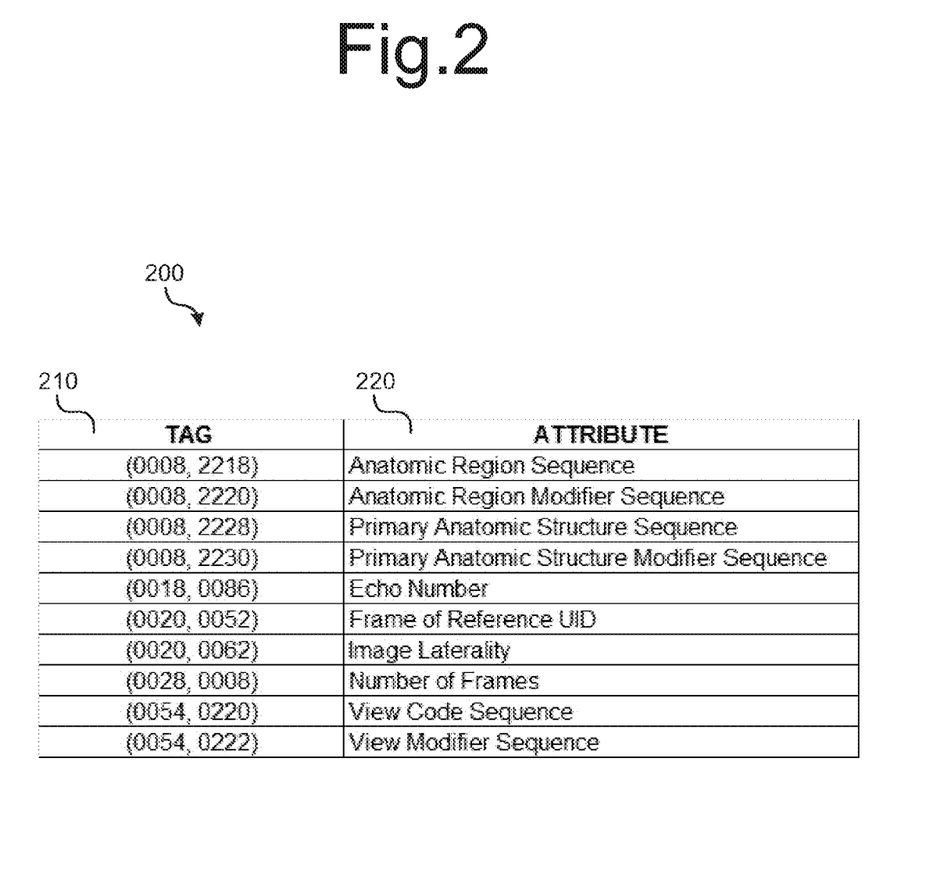
FIG. 2 is an example table illustrating example attribute names and their associated tag identifier for a DICOM object.

FIG. 2 is a an example table 200 illustrating example attributes 220 that may be associated with a DICOM object of image series 220, and their associated tag identifier 210. For example, a tag for an anatomic structure or region that has been exposed to ionizing radiation may be expressed as (0008, 2229). As another example, a tag for the number of frames in an image series 120 may be expressed as (0028, 0008).

In example communications environment 110, the generated DICOM imaging series 120 is subsequently transmitted via communication medium 130 to a DICOM server 140. The medium 130 may comprise a wireless network system such as a cellular network, a satellite network, a wireless local area network, a Bluetooth system, or the like. The medium may additionally comprise a wired network system, such as a coaxial cable system, a fiber optic cable system, an Ethernet cable system, a USB system, or the like.

DICOM server 140 stores received DICOM image series 120 and other information associated with the series in a DICOM storage. In one example embodiment, DICOM server 140 may comprise a connectivity interface for interfacing via communication medium 130, a security module for authenticating access to the DICOM image series 120, a DICOM storage for storing the image series 120, and a DICOM database. In this embodiment, the DICOM database may perform administrative functions related to the administration and retrieval of stored DICOM image series and other information, including the management of the DICOM storage and security module.

In this example environment, Server 140 makes the imaging series 120 available to an authorized DICOM computer 150 for display, analysis, and sorting using the methods disclosed herein. In alternative embodiments, the DICOM image series 120 captured at medical modality 110 may be directly provided to the operator of DICOM computer 150. For example, DICOM image series 120 may be provided on a portable digital recording medium such as a flash drive, CD, DVD, or Blu-Ray disc. As another example, the DICOM image series 120 may be made available for download via a secure online portal that requires a secured login of an authorized viewer of the DICOM image series. In yet another example, the image series may be emailed.

Figure 3:
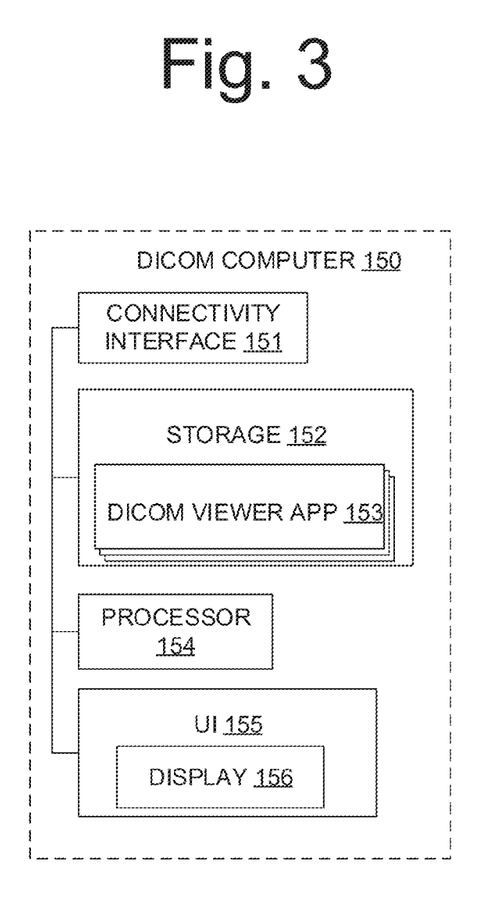
FIG. 3 is a block diagram illustrating an exemplary DICOM computer that may be used implement the methods disclosed herein.

Example DICOM computer 150 is any computing device (workstation, laptop, tablet, smartphone etc.) configured to receive DICOM image series 120 and implement a user-configurable rules based engine for a DICOM viewing application that automatically splits DICOM image series 120 into framesets. As illustrated in FIG. 3, example DICOM computer 150 comprises a connectivity interface 151 for connecting to communication medium 130 for access image series 120, storage 152 for storing DICOM viewer application 153, processor 154 and user interface 155 that includes a display 156 for allowing an operator to view the DICOM images of the DICOM image series.

During operation, an operator of DICOM computer 150 executes DICOM viewer application 153 using processor 154. DICOM image series 120 may then be sorted and displayed on display 156 using viewer application 153. As further described below, for display purposes, DICOM image series 120 is subdivided into framesets by applying a user-configurable rules based engine that automatically splits and orders DICOM image series 120 according to user-selected DICOM tags.

Figure 4:
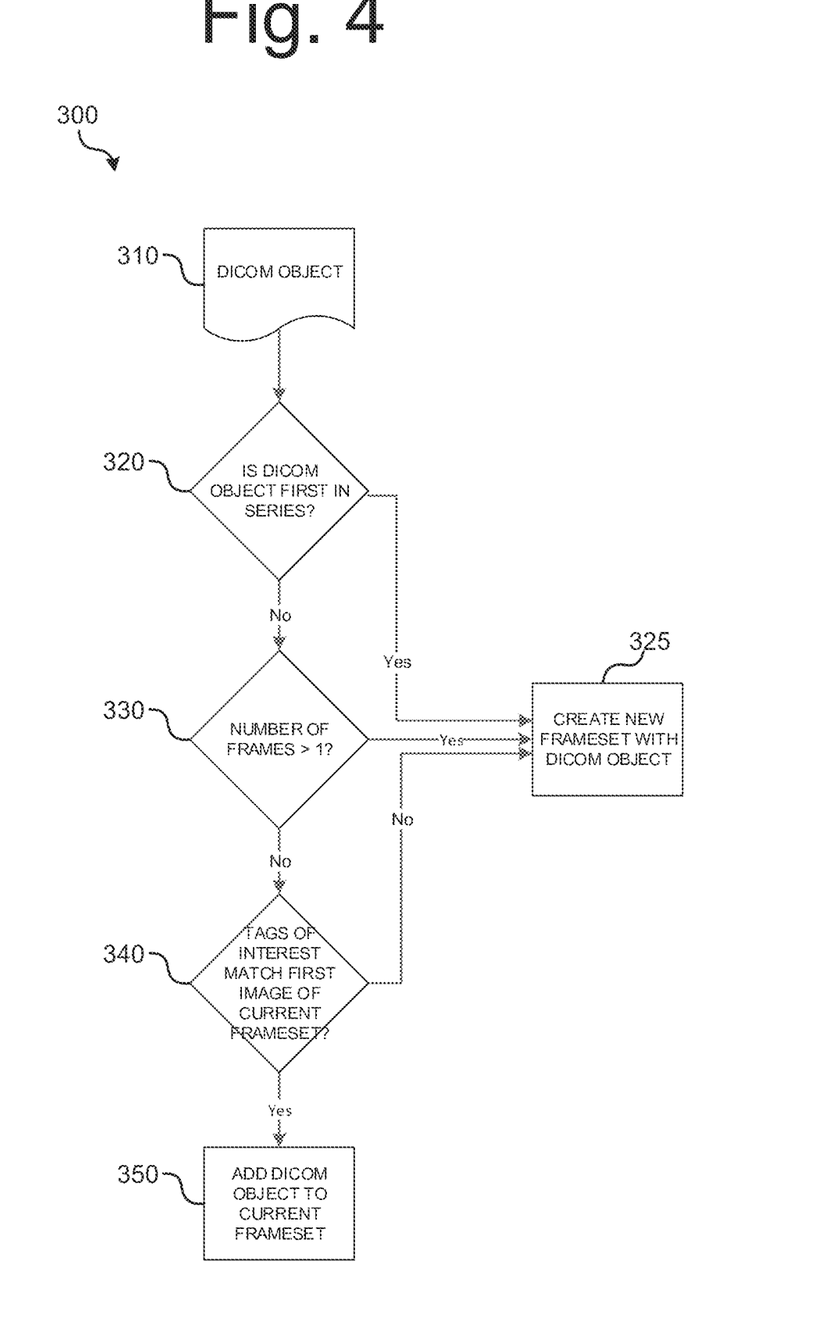
FIG. 4 is an operational flow diagram illustrating an exemplary process for splitting a medical image series corresponding to a DICOM Object into one or more framesets.

FIG. 4 is an operational flow diagram illustrating an exemplary process 300 that is implemented by DICOM viewer application 153 to provide this functionality. As illustrated, process 300 may applied to one or more DICOM image objects 310 of DICOM image series 120 to subdivide image series 120 into one or more framesets according to user-specified DICOM tags. Prior to implementing process 300, a user predefines DICOM tags of interest that are made unique for all frames (images) within a frameset. As one example, consider the tags 210 of table 200. In one embodiment, a user may require tags 210 to all be the same for each frame in a frameset.

With reference now to process 300, at operation 320 it is determined if DICOM object 310 is the first DICOM image object in image series 120. If it is the first image object, at operation 325 a new frameset is created for DICOM image object 310. Alternatively, if it is not the first object, at operation 330 it is determined if the number of frames in DICOM object 310 is greater than 1. If there are multiple frames in DICOM image object 310, then a new frameset is created for DICOM image object 310 (operation 325). Otherwise, process 300 proceeds to operation 340. At operation 340, it is determined if the tags of interest predefined by the user (e.g. the tags of table 200) match the first image of the current frameset. If not all the tags of interest match, then a new frameset is created for DICOM image object 310 (operation 325). Otherwise, at operation 350 the DICOM object is added to the current frameset. Process 300 may iteratively repeat for all DICOM objects 310 of image series 120, thereby splitting the image series into framesets based on the user predefined DICOM tags.

In various embodiments, DICOM image series tag splitting rules may be customized for different purposes. For example, in one embodiment the tag-based rules may be configured depending on whether a display, transmission, storage, or other function is performed on DICOM image series 120. In another embodiment, the rules may be predetermined based on a particular physician or facility preference for tag-based image series splitting.

In other embodiments, the tag splitting rules may specify different hierarchies of desired matching. For example, in one embodiment a hierarchy of required tags and desired tags may be specified. In this example embodiment, a two-stage process may be executed where framesets are 1) first grouped based on required matching tags, and 2) subsequently grouped based on desired matching tags (if there are matches).

Process 300 addresses the problem of conventional processes implemented by conventional DICOM viewer applications. Many modality devices send somewhat unrelated DICOM image instances within a single series. Displaying these images as a single frameset may not be desirable for a physician to review the images. Conventionally, each multi-frame DICOM image is normally separated into its own frameset, whereas a set of single frame DICOM images are normally grouped into a single frameset. However, this simple separation of series into framesets may not correctly group clinically relevant images correctly into a frameset. For example, multi-echo MR series may need to be separated into different framesets based on different echo number attributes. Additionally, a physician may desire an image series containing different anatomical views, laterality, frame of reference, or based on any other image specific clinically relevant criteria to be separated into different framesets such that only those frames containing identical values for all of these tags are included in a single frameset.

Figure 5:
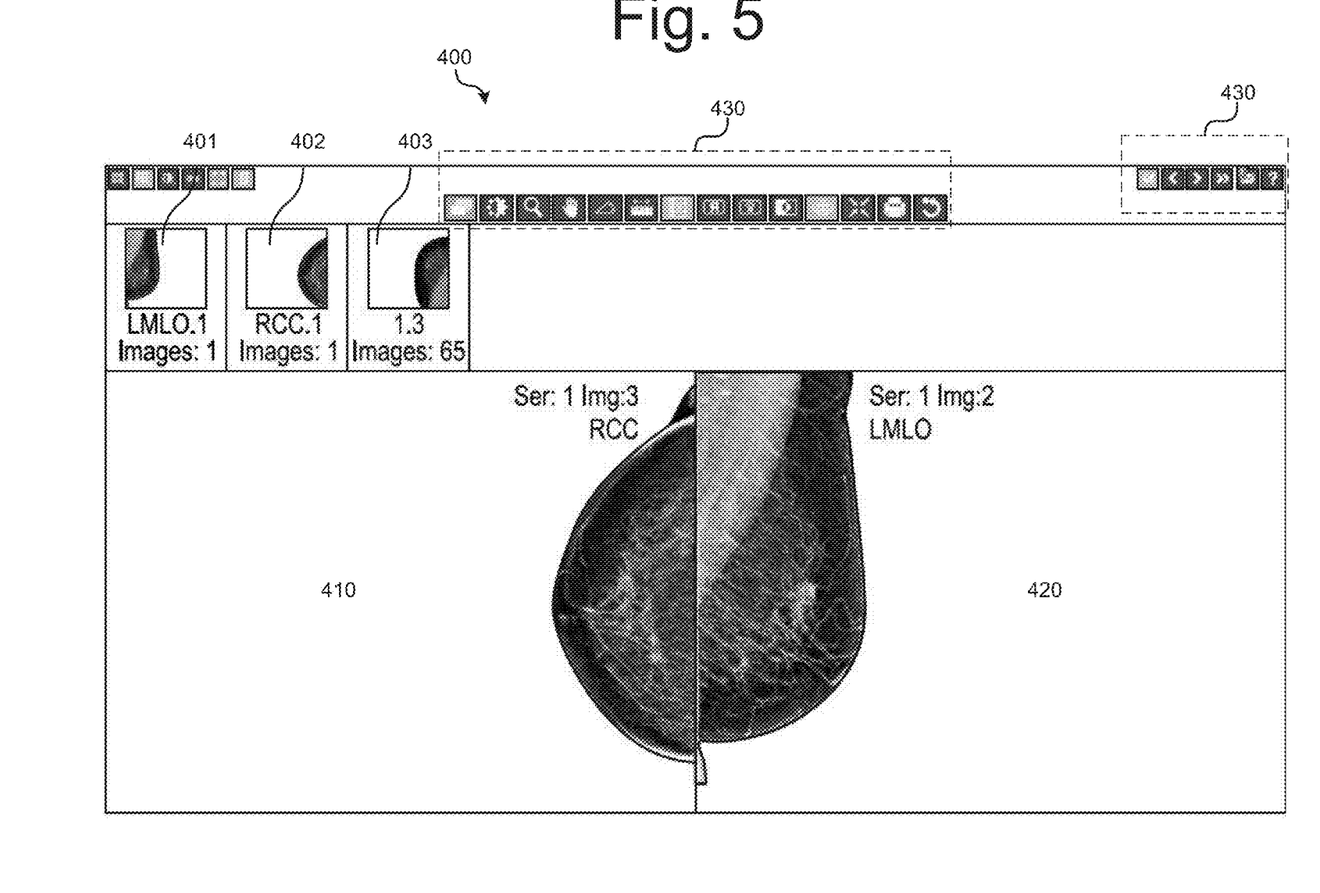
FIG. 5 illustrates a particular implementation of an example graphical user interface that may be used by a user of a DICOM computer to split a DICOM image series using the process of FIG. 4.

FIG. 5 illustrates a particular implementation of an example graphical user interface (GUI) 400 that may be used by a user of DICOM computer 150 to split a DICOM image series using method 300. In embodiments, GUI 400 may be displayed on display 156 by executing DICOM viewer application 153.

As illustrated in this particular embodiment, interface 400 displays the results of using method 300 to split a mammography DICOM image series into three user-selectable frame sets 401-403. In this example, the mammography DICOM image series is split based on the DICOM Tag (0054, 0220) View Code Sequence (i.e., each image of a frame set must have the same View Code Sequence tag). As would be understood by one having skill in the art, the DICOM Tag "View Code Sequence" describes the radiographic view of a DICOM image relative to the orientation of the imaged patient. In this example, the first frame set 401 corresponds to a left mediolateral oblique (LMLO) mammographic view. The second frame set 402 corresponds to a right cranio-caudal (RCC) mammographic view. Additionally, each of selectable frame sets 401-403 includes identifiers specifying the number of images corresponding to the frame set and a name associated with the frame set. In embodiments, the name associated with the frame set may be based on the DICOM Tag used to split the frame set from an image series. GUI 400 additionally includes a set of controls 430 (e.g., buttons, toggles, sliders, navigational components, etc.) for loading, selecting, viewing, labeling, analyzing, and performing other like operations on displayed images of the framesets split from the DICOM image series.

Interface 400 provides a tiled window interface for visualizing selected images of each frame set 401-403. A first window 410 displays an LMLO mammographic image corresponding to the LMLO frame set 401. A second window 420 displays an LMLO mammographic image corresponding to the RCC frame set 402. In various embodiments, any number of tiled windows may be used to display images corresponding to different frame sets that were split from an image series. Alternatively, in other embodiments, the tiled windows may be used to display multiple images corresponding to one frame set.

Figure 6:
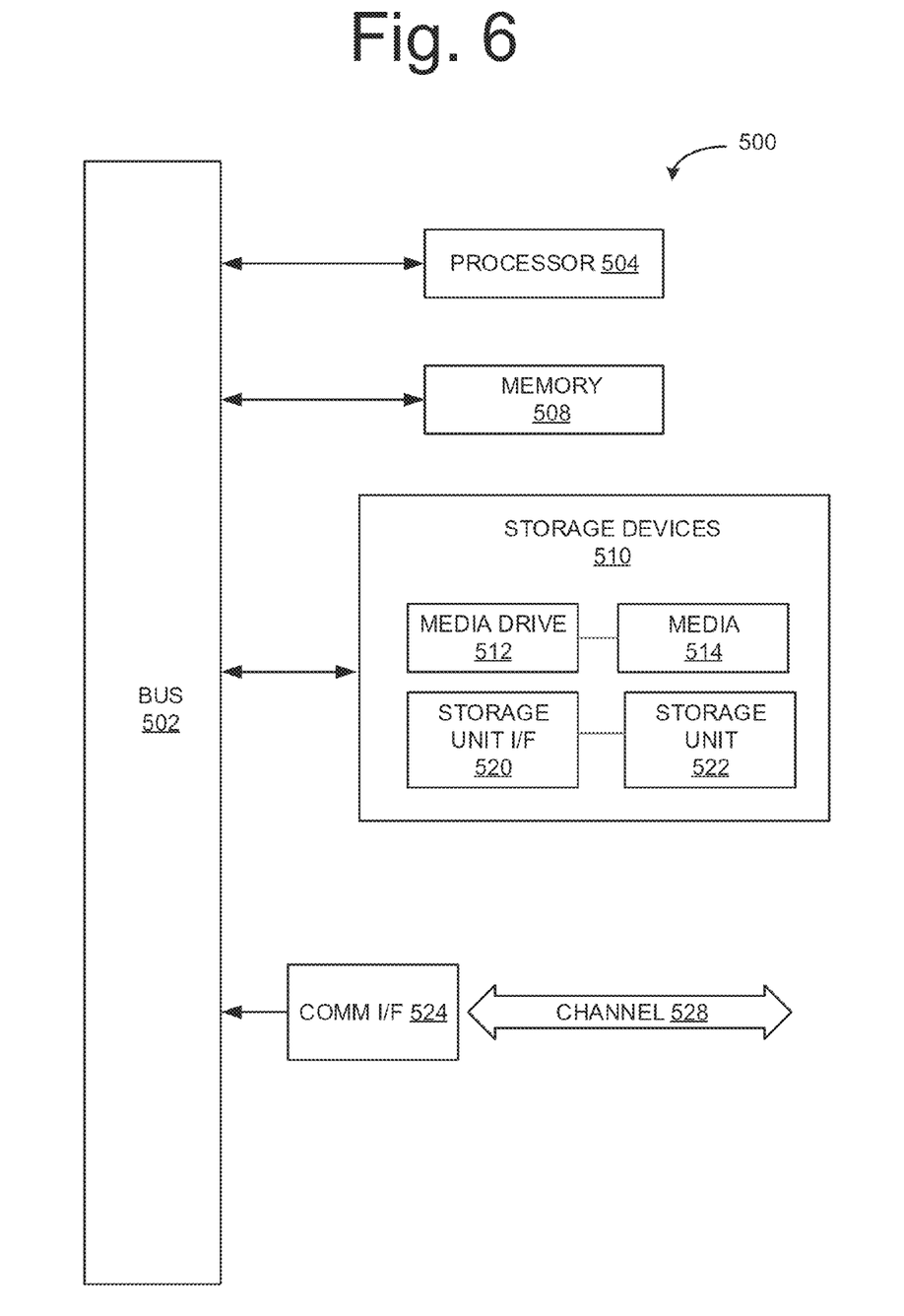
FIG. 6 is an example computing module that may be used to implement various features of the systems and methods disclosed herein.

FIG. 6 illustrates an example computing module that may be used to implement various features of the system and methods disclosed herein.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 6. Various embodiments are described in terms of this example-computing module 500. After reading this description, it will become apparent to a person skilled in the relevant art how to implement the application using other computing modules or architectures.

Referring now to FIG. 6, computing module 500 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 500 might include, for example, one or more processors, controllers, control modules, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing module 500 or to communicate externally.

Computing module 500 might also include one or more memory modules, simply referred to herein as main memory 508. For example, preferably random access memory (RAM) or other dynamic memory, might be used for storing information and instructions to be executed by processor 504. Main memory 508 might also be used for storing temporary variables or other intermediate information during execution of instructions to be executed by processor 504. Computing module 500 might likewise include a read only memory ("ROM") or other static storage device coupled to bus 502 for storing static information and instructions for processor 504.

The computing module 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a solid state drive, a magnetic tape drive, an optical disk drive, a CD, DVD, or Blu-ray drive (R or RW), or other removable or fixed media drive might be provided. Accordingly, storage media 514 might include, for example, a hard disk, an integrated circuit assembly, magnetic tape, cartridge, optical disk, a CD, DVD, Blu-ray Disc, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing module 500. Such instrumentalities might include, for example, a fixed or removable storage unit 522 and an interface 1020. Examples of such storage units 522 and interfaces 520 can include a program cartridge and cartridge interface, a removable memory (for example, a flash memory or other removable memory module) and memory slot, a PCMCIA slot and card, and other fixed or removable storage units 522 and interfaces 520 that allow software and data to be transferred from the storage unit 522 to computing module 500.

Computing module 500 might also include a communications interface 524. Communications interface 524 might be used to allow software and data to be transferred between computing module 500 and external devices. Examples of communications interface 524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 500 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A system for splitting a Digital Imaging and Communications in Medicine (DICOM) medical image series into framesets, comprising:
one or more processors; and
one or more non-transitory computer-readable mediums operatively coupled to at least one of the one or more processors and having instructions stored thereon that, when executed by at least one of the one or more processors, cause the system to:
determine that a DICOM image object of the DICOM medical image series is not a first DICOM object of the medical image series;
determine that the DICOM image object does not have more than one image frame;
determine whether a first predefined DICOM tag of interest of the DICOM image object matches a first DICOM tag of interest of a first image of a first frameset; and
when it is determined that the first predefined DICOM tag of interest of the DICOM image object matches the first DICOM tag of interest of the first image of the frameset, the instructions when executed by at least one of the one or more processors, further cause the system to add the DICOM image object to the first frameset.

2. The system of claim 1, wherein when it is determined that the first predefined DICOM tag of interest of the DICOM image object does not match the first DICOM tag of interest of the first image of the frameset, the instructions when executed by at least one of the one or more processors, further cause the system to create a second frame set including the DICOM image object.

3. The system of claim 1, wherein the instructions when executed by at least one of the one or more processors, further cause the system to determine whether a second predefined DICOM tag of interest of the DICOM image object matches a second DICOM tag of interest of the first image of the first frameset.

4. The system of claim 3, wherein prior to determining whether the first and second predefined DICOM tags of interest of the DICOM image object match the respective first and second DICOM tags of interest of the first image of the first frameset, the instructions when executed by at least one of the one or more processors, further cause the system to display a graphical user interface whereby a user selects the first and the second DICOM tags of interest.

5. A system for splitting a Digital Imaging and Communications in Medicine (DICOM) medical image series into framesets, comprising:
one or more processors; and
one or more non-transitory computer-readable mediums operatively coupled to at least one of the one or more processors and having instructions stored thereon that, when executed by at least one of the one or more processors, cause the system to:
determine that a DICOM image object of the DICOM medical image series is not a first DICOM object of the medical image series;
determine that the DICOM image object does not have more than one image frame;
determine whether a first predefined DICOM tag of interest of the DICOM image object matches a first DICOM tag of interest of a first image of a first frameset; and
wherein prior to determining that a DICOM image object of the DICOM medical image series is not the first DICOM object of the medical image series, the instructions when executed by at least one of the one or more processors, cause the system to:
determine that a first DICOM image object of the DICOM medical image series is the first DICOM object of the medical image series; and
create the first frame set including the first DICOM image object in response to determining that the first DICOM image object is the first DICOM object of the medical image series.

6. The system of claim 5, wherein the instructions when executed by at least one of the one or more processors, further cause the system to:
determine that a third DICOM image object of the DICOM medical image series is not a first DICOM object of the medical image series;
determine that the third DICOM image object has more than one image frame; and
in response to determining that the third DICOM image object has more than one image frame, creating a second frame set including the third DICOM image object.

7. The system of claim 6, wherein the instructions when executed by at least one of the one or more processors, further cause the system to display on a display a graphical user interface including a control for selecting the first frame set and a control for selecting the second frame set.

8. The system of claim 7, wherein the instructions when executed by at least one of the one or more processors, further cause the system to:
receive user input at the system actuating the control for selecting the second frame set; and
in response to receiving the user input, displaying an image of the second frame set on the graphical user interface.

9. A method for splitting a Digital Imaging and Communications in Medicine (DICOM) medical image series into framesets, comprising:
receiving the DICOM medical image series at a non-transitory computer readable medium; and
one or more processors:
determining that a DICOM image object of the DICOM medical image series is not a first DICOM object of the medical image series;
determining that the DICOM image object does not have more than one image frame;
determining whether a first predefined DICOM tag of interest of the DICOM image object matches a first DICOM tag of interest of a first image of a first frameset; and
the one or more processors adding the DICOM image object to the first frameset when it is determined that the first predefined DICOM tag of interest of the DICOM image object matches the first DICOM tag of interest of the first image of the frameset.

10. The method of claim 9, further comprising: the one or more processors creating a second frame set including the DICOM image object when it is determined that the first predefined DICOM tag of interest of the DICOM image object does not match the first DICOM tag of interest of the first image of the frameset.

11. The method of claim 9, further comprising: the one or more processors determining whether a second predefined DICOM tag of interest of the DICOM image object matches a second DICOM tag of interest of the first image of the first frameset.

12. The method of claim 11, further comprising: displaying a graphical user interface whereby a user selects the first and the second DICOM tags of interest prior to determining whether the first and second predefined DICOM tags of interest of the DICOM image object match the respective first and second DICOM tags of interest of the first image of the first frameset.

13. A method for splitting a Digital Imaging and Communications in Medicine (DICOM) medical image series into framesets, comprising:
  receiving the DICOM medical image series at a non-transitory computer readable medium; and
  one or more processors:
    determining that a DICOM image object of the DICOM medical image series is not a first DICOM object of the medical image series;
    determining that the DICOM image object does not have more than one image frame;
    determining whether a first predefined DICOM tag of interest of the DICOM image object matches a first DICOM tag of interest of a first image of a first frameset; and
    wherein prior to determining that a DICOM image object of the DICOM medical image series is not the first DICOM object of the medical image series, the method further comprises:
      determining that a first DICOM image object of the DICOM medical image series is the first DICOM object of the medical image series; and
      creating the first frame set including the first DICOM image object in response to determining that the first DICOM image object is the first DICOM object of the medical image series.

14. The method of claim 13, further comprising the one or more processors:
  determining that a third DICOM image object of the DICOM medical image series is not a first DICOM object of the medical image series;
  determining that the third DICOM image object has more than one image frame; and
  in response to determining that the third DICOM image object has more than one image frame, creating a second frame set including the third DICOM image object.

15. The method of claim 14, further comprising displaying on a display a graphical user interface including a control for selecting the first frame set and a control for selecting the second frame set.

16. The method of claim 15, further comprising:
  receiving user input through the graphical user interface actuating the control for selecting the second frame set;
  in response to receiving the user input, displaying an image of the second frame set on the graphical user interface.

17. A system for splitting a Digital Imaging and Communications in Medicine (DICOM) medical image series into framesets, comprising:
  one or more processors; and
  one or more non-transitory computer-readable mediums operatively coupled to at least one of the one or more processors and having instructions stored thereon that, when executed by at least one of the one or more processors, cause the system to:
    determine that a first DICOM image object of the DICOM medical image series is the first DICOM object of the medical image series;
    create a first frame set including the first DICOM image object in response to determining that the first DICOM image object is the first DICOM object of the medical image series;
    determine that a predefined DICOM tag of interest of a second DICOM image object of the DICOM medical image series matches a DICOM tag of interest of an image of the first created frameset; and
    add the second DICOM image object to the first frameset in response to determining that the predefined DICOM tag of interest of the second DICOM image object matches the DICOM tag of interest of the image of the first created frameset.

18. The system of claim 17, wherein the instructions when executed by at least one of the one or more processors, further cause the system to:
  determine that a third DICOM image object of the DICOM medical image series has more than one image frame; and
  in response to determining that the third DICOM image object has more than one image frame, create a second frame set including the third DICOM image object.

* * * * *